United States Patent

Klatzmann et al.

Patent Number: 6,004,803
Date of Patent: Dec. 21, 1999

[54] GENES ENCODING HSV1-TK CONTAINING A DELETION OF 5' CRYPTIC PROMOTER SITES, VECTORS AND CELL LINES

[75] Inventors: David Klatzmann, Paris; Benoit Salomon, Villejuif, both of France

[73] Assignee: Universite Pierre et Marie Curie (Paris VI), Paris Cedex, France

[21] Appl. No.: 08/793,518

[22] PCT Filed: Aug. 17, 1995

[86] PCT No.: PCT/FR95/01098

§ 371 Date: Apr. 11, 1997

§ 102(e) Date: Apr. 11, 1997

[87] PCT Pub. No.: WO96/06176

PCT Pub. Date: Feb. 29, 1996

[30] Foreign Application Priority Data

Aug. 25, 1994 [FR] France .................. 94 10298

[51] Int. Cl.$^6$ .......... C12N 15/00; C12N 15/86; C12N 5/00; C07H 21/04
[52] U.S. Cl. ............ 435/320.1; 435/325; 435/456; 435/457; 536/23.2
[58] Field of Search ............... 435/320.1, 325, 435/172.3, 456, 457; 424/93.2; 536/23.2

[56] References Cited

FOREIGN PATENT DOCUMENTS 10494776  7/1992  European Pat. Off. .
WO 9413824  6/1994  WIPO .

OTHER PUBLICATIONS

Kappel et al (1992) Current Opin. Biotech. 3, 548–553.
Mullen (1994) Pharm. Ther. 63, 199–207.
Zemskova et al (1991) Gene 106, 249–253.
Burns et al (1993) Proc. Natl. Acad. 90, 8033–8037.
Culver et al (1992) Science 256, 1550–1552.
Salomon et al., *Molecular and Cellular Biology*, vol. 15, No. 10, pp. 5322–5328 (Oct. 1995).

*Primary Examiner*—Deborah Crouch
*Attorney, Agent, or Firm*—Birch, Stewart, Kolasch & Birch, LLP

[57] ABSTRACT

A recombinant vector comprising a gene encoding a Herpes Simplex Virus Type 1 thymidine kinase (HSV1-TK) comprising a deletion in the 5' sequence upstream of the second ATG initiation codon of the complete HSV1-TK sufficient to inhibit transcription initiation from a cryptic promoter site contained within the 5' sequence, wherein the gene is under the control of a promoter is disclosed for use as a suicide gene both in vitro and in vivo. The HSV1-TK produced by the strong expression of the modified gene is toxic to cells in the presence of nucleoside analogs, whereas weak expression of the gene is not toxic to cells. The deletion can comprise all or part of the first initiation codon and the vector can be a retrovirus. As also disclosed are cells transduced with the vector.

17 Claims, 5 Drawing Sheets

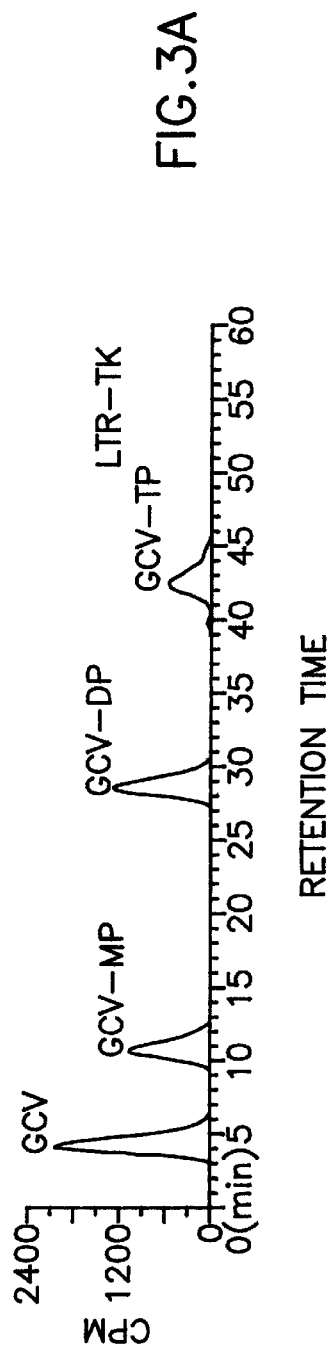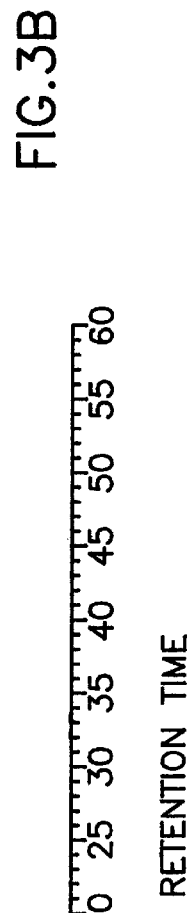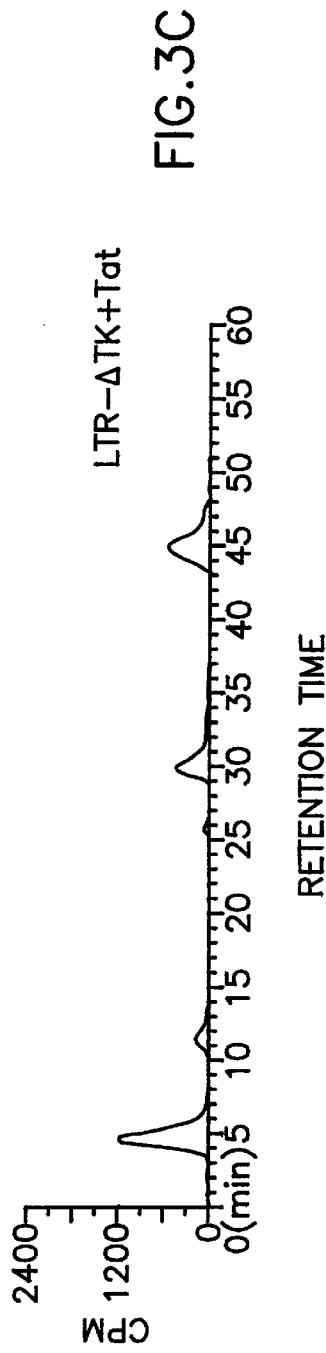

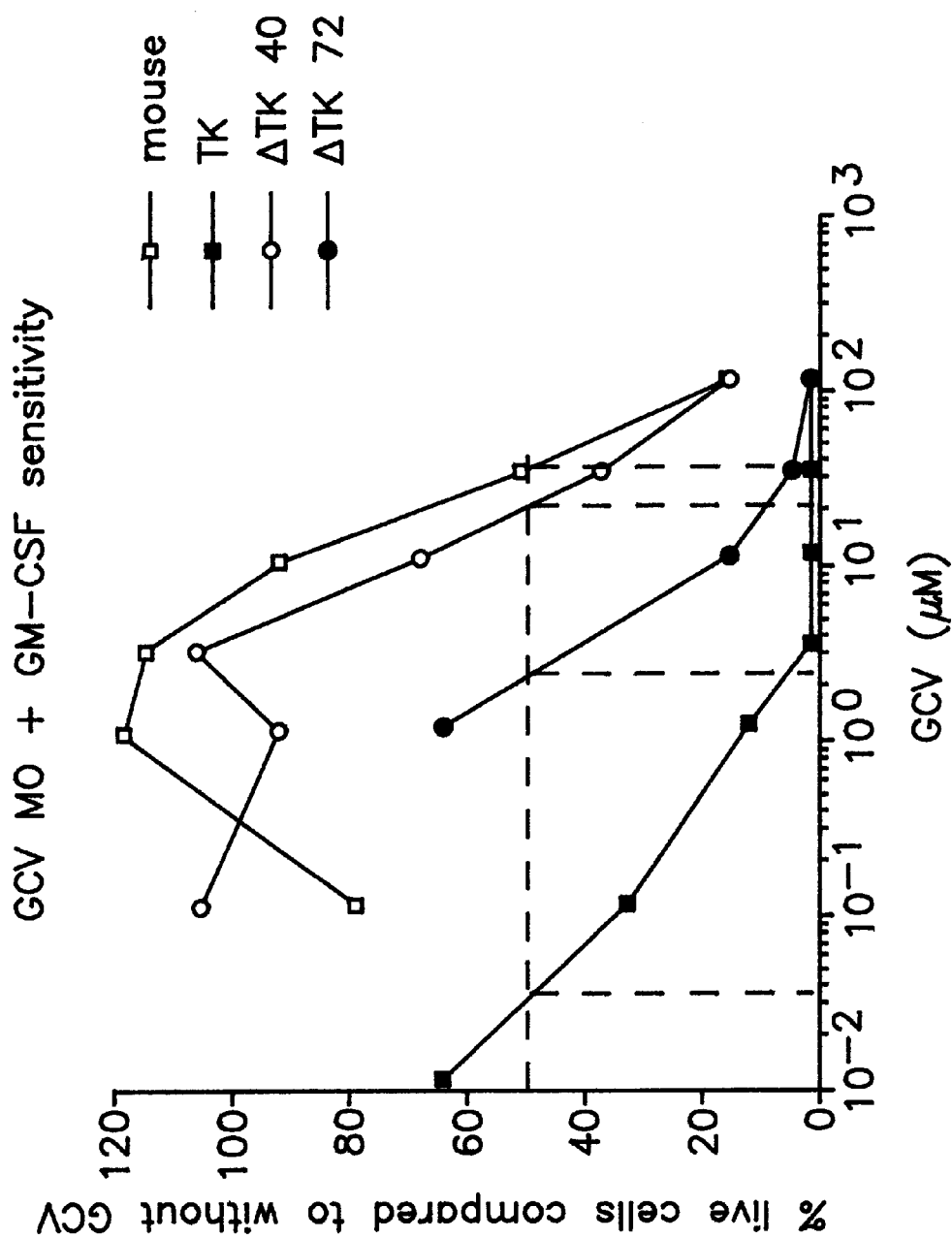

□ Control mice
■ Transgenic mice
● Double transgenic mice
▲ Transgenic mice

GENES ENCODING HSV1-TK CONTAINING A DELETION OF 5' CRYPTIC PROMOTER SITES, VECTORS AND CELL LINES

The present invention relates to an improvement made in the medicaments used in suicide gene-based gene therapy, and in particular in all the medicaments using the system for expression of a thymidine kinase gene in cells infected with a virus or in cancer cells, making said cells specifically sensitive to nucleoside analogs (N.A.) especially ganciclovir (GCV) or aciclovir (ACV).

The Herpes simplex virus type I thymidine kinase (HSV1-TK) gene has acquired a considerable importance in the developments of antiviral or anticancer therapy using a conditional toxicity and HSV1-TK is the enzyme which has been the subject of the largest number of investigations relating to suicide genes.

This enzyme, which is atoxic for eukaryotic cells, exhibits the characteristic of being able to convert certain nucleoside analogs such as ACV or GCV to monophosphate-containing molecules, of which cellular kinases are normally incapable (1,2). These monophosphate-containing nucleosides are then converted by cellular enzymes to nucleoside triphosphates which are used during the synthesis of DNA and block the extension process, thus causing the death of the cell.

Other viral thymidine kinases having the same properties can also be used, especially that of the varicella-zoster virus (VZV) as described in patent application EP 415 731. In the text which follows, where reference is made to HSV1-TK, persons skilled in the art will know how to generalize it to equivalent enzymes.

This conditional toxicity of HSV1-TK was first demonstrated in vitro and is now used in vivo for several purposes including:

gene therapy by destruction of diseased cells: cancerous cells or cells infected by viruses and especially retroviruses (4,7,8), removal of specific cell types such as lymphocytic cells, or growth hormone secreting cells, or dendritic cells (D.C.) (10) in transgenic animal lines having the HSV1-TK gene under the control of specific cellular promoters; this system is a very powerful research means to know the physiological rose of either of these cellular types.

In antiviral therapy, it is the transactivation, under the effect of a viral infection, of a promoter regulating the synthesis of HSV1-TK which increases the synthesis of thymidine kinase, whose toxic effect manifests itself in the presence of an N.A.

All the advantages which may be gained from the use of this type of conditional toxins can therefore be understood when applied to gene, especially anticancer or antiviral, therapy.

Firstly, only a conditional toxicity makes it possible to generate stable cellular clones producing the pseudo-viral particles capable of producing such a transgene and transferring the suicide gene into the target cells. Indeed, these cells simply have to be cultured in the absence of ACV or GCV since HSV1 thymidine kinase is not toxic for the cell in the absence of these drugs.

Next, in the event of a side effect of the treatment in the patient, stopping the administration of ACV or GCV causes the toxicity due to the transgene to cease immediately; in addition, an adjustment of the doses of the nucleoside analog makes it possible to selectively destroy the cells strongly expressing the transgene while preserving as much as possible the cells in which the gene is weakly expressed. Finally, the toxicity which is restricted to dividing cells is a great advantage especially for the treatment of cancer cells.

Finally, experimental data in vitro and in vivo have shown that cells not expressing HSV1-TK, but which are in contact with those expressing it, were also destroyed by the treatment with ACV ("metabolic cooperation" or "bystander effect") (3,4).

The mechanism of this effect is still not understood, but it is possible that the nucleoside triphosphate analogs can pass from one cell to another via "gap junctions" or intercellular communications.

In a transfer of exogenous genes in eukaryotic cells, especially human cells, the retroviruses appear to be the preferred vectors. However, an essential prerequisite for their use for therapeutic purposes is to ensure the safety of their use: the present invention offers a means of increasing the safety of the system without decreasing the therapeutic index of the treatment with an N.A. by administration of recombinant retroviruses containing a gene encoding thymidine kinase, said gene being modified by deletion or mutation in its 5' part such that the gene expresses a kinase activity which is nontoxic in the presence of GCV if it is weakly expressed and which is toxic if it is strongly expressed.

The therapeutic index is defined as the ratio of the lethal doses 50% (LD50) for the treatment with N.As of cells containing the suicide gene to those which does not contain it; in some cases, the therapeutic index may be increased if the cells expressing the suicide gene at a low level remain insensitive to the toxic effect of the N.As In the case of cancer cells, the safety of the system is provided by the use of packaging cells which produce only defective retroviruses, thus avoiding the spread of a reconstituted wild-type virus in the cell population or the tissue treated; the development of such packaging cell lines has considerably increased the use of retroviruses in gene therapy; in this case, the actual viral vector preserves the essential sequences; the LTRs for the control of reverse transcription and integration, the ψ sequence necessary for encapsidation, the TB sequence necessary for the viral replication; the viral genes (gag, pol, env) are deleted and replaced by the thymidine kinase gene placed under the control of its own promoter or a promoter judged to be more powerful, specific or regulatable. The viral genes gag, pol, env are often integrated into another vector, sometimes called Helper and which is defective for the LTR and ψ sequences. Their expression allows the encapsidation of the transgene, excluding the genes necessary for the multiplication of the viral genome and for the formation of complete viral particles.

The proviral form the Helper is in general integrated into the genome of a murine cell line (for example the fibroblast line NIH/3T3) which acts both as host for the vector and Helper for the functions which it lacks. After transfection of the vector, the cellular strain becomes capable of producing defective infectious viral particles. However, these particles contain only the transgene (HSV1-TK) but do not contain the information necessary for the reconstitution of complete viral particles in the target cells. This system is therefore designed normally to prevent any subsequent propagation of virus after the first infection, that is to say if the virus carrying the transgene penetrates into a cell lacking the information of the Helper type (gag, pol, env), its production is stopped.

Different packaging systems allowing the production of defective recombinant viruses capable of infecting dividing cells have been described, especially in patent applications EP 0 243 204, WO 89/07150, WO 90/02806, WO 90/12087, EP 0 476 953, WO 93/04167 and WO 93/10218.

Likewise, Caruso M. et al. (8) and Yves Panis et al., (9) have been able to demonstrate an effect by direct injection of murine fibroblasts producing recombinant retroviral particles expressing the HSV1-TK gene.

Finally, a new system was recently developed which allows the expression of a transgene in a target cell or a human or animal tissue, this system being characterized in that it consists of a eukaryotic cell established as a line into which were transfected:

on the one hand, a recombinant pseudo-retroviral sequence in which the env gene has been deleted in its entirety or partially and substituted by said transgene at the level of the env gene, such that the transgene in question is expressed on transcripts similar to those of the wild-type virus, except that the env protein is substituted by the HSV1-TK protein, on the other hand, a nucleic acid sequence including a sequence encoding an envelope or membrane protein, which sequence is under the control of a promoter and is associated, where appropriate, with said transgene and flanked at its 3' end by a polyadenylation site, the recombinant viral genome and the nucleic acid sequence including the sequence for the env protein being capable of transcomplementation and of allowing the host cell to produce defective infectious viruses having the envelope protein but lacking the corresponding gene. This system, which is the subject of patent application FR 9401994 is particularly advantageous when the transgene to be expressed is a suicide gene of the HSV1-TK type. This system allows the production, in a first instance, of infectious viral particles carrying especially the HSV1-TK gene but lacking themselves the envelope gene, this leading to an abortive infectious cycle from the second infection onwards.

A therapeutic target of the HSV1-TK/N.A. system consists of cells infected or capable of being infected by a virus, especially the HIV retrovirus. These cells are, in contrast to cancer cells, cells which divide little and are therefore not very likely to be infected directly and with good efficiency by a retroviral vector; the cells in question are then infected by a construct containing the thymidine kinase gene under the control of the HIV LTR, this construct being itself included in a recombinant retrovirus which ensures the transduction thereof with the required efficiency. In this case, the cells, after infection by a retrovirus such as HIV, produce the LTR transactivating signals, bringing about the expression of the thymidine kinase gene and making the cells sensitive to the N.As then administered as medicaments (5). In this case, it is indeed the infection itself by the virus which will trigger the expression of the killer gene and confer on the cell a specific sensitivity to ganciclovir or aciclovir.

It is essential in both cases that the suicide genes, under the control of a specific promoter, are regulated such that the whole treatment combining the transfection of the cells by the vector carrying the thymidine kinase gene with the administration of the medicaments of the aciclovir or ganciclovir type will not in any case affect healthy cells, and it is the aim of the present invention to add an additional safety element.

In the case, for example, of the treatment of HIV infection, the transgene will have to be introduced into the hematopoietic stem cells and expressed, if possible, exclusively in the differentiated cells which will be derived therefrom, in particular the T lymphocytes, the monocytes and the dendritic cells. Furthermore, as seen above, it will be necessary that this gene is activated only in the presence of an infection by the retrovirus, such that only the infected cells are destroyed by administration of GCV or ACV. However, it has been shown that in the absence of HIV infection, the HIV LTR still has a weak but real basal expression (6).

This basal expression may be problem with some suicide genes and some nucleoside analogs; for example, lymphoid cells which express the HSV1-TK gene under the control of the HIV LTR weakly and continuously express this gene, which does not make it possible to use ganciclovir as nucleostide analog because the latter proves to be much too toxic. In contrast, as regards aciclovir, this drug may be used at a concentration of 10 microMolar which preserves the uninfected cells and which makes it possible to kill the infected cells (7).

This basal expression of HSV1 thymidine kinase limits the therapeutic index of the N.A. used and it is not possible, using this system, to increase the concentrations and aciclovir above 10 microMolar, which, in certain cases, may be highly desirable.

The "bystander" or metabolic cooperation effect described above could have the consequence of making the N.As toxic for cells in the vicinity of the target cells, but which are not initially targeted, conferring side effects on the treatment, one of the ways of decreasing this "bystander" effect is to include in the construct a promoter which is specific for the tissue or the cells which are the targets of the treatment. However, a residual expression of thymidine kinase may continue to exist even under the control of a specific promoter in the tissues or in the cells transfected by the plasmid.

In this type of situation, it is important that the suicide gene which is weakly expressed is well tolerated during a treatment with aciclovir or ganciclovir, but which, when its expression is activated, for example by transactivation during an HIV infection, proves as toxic as the wild-type HSV1-TK gene.

The present invention relates to a recombinant vector carrying a suicide gene under the control of a promoter and capable, when it is expressed in cells transformed by said vector, of phosphorylating nucleoside analogs such as aciclovir or ganciclovir, leading to the death of the cell by blocking replication, said vector being characterized in that the suicide gene is the Herpes Simplex virus type 1 thymidine kinase (HSV1-TK) gene deleted in its 5' part of all or part of the 5' sequence upstream of the second ATG codon corresponding to methionine 46 of the complete protein, in particular when the deletion includes all or part of the 1st initiation codon corresponding to methionine No. 1.

The present invention results from the discovery according to which the $HSV_1$-TK gene contains, between the first two ATG codons, a cryptic promoter and several sites for initiation of transcription leading, in some situations, to the synthesis of thymidine kinase which is functional and truncated in its N-terminal part.

It has been shown, indeed, that transgenic male mice having the HSV1-TK gene as transgene with conditional toxicity for destroying certain cellular categories and studying the effects thereof, became sterile, making their reproduction impossible; this sterility was due (15) to a hyper expression of the HSV1-TK gene in the testicles accompanied by the formation of transcripts which were shorter and were initiated in the coding sequence of HSV1-TK. Subsequent experiments showed that this cryptic promoter of the HSV1-TK gene was activated specifically in the testicles leading to this hyper production of HSV-TK which is truncated and which is nevertheless functional (15).

In the use of plasmids carrying HSV1-TK as suicide genes in the presence of N.A., the conditional toxicity of HSV1-TK depends on the quantity both of the nucleoside analogs and on the enzyme synthesized by the HSV1-TK gene. What is surprising in the construct of the invention is that it not only makes it possible to express, using the truncated HSV1-TK gene, a kinase activity but that, in addition, this activity makes it possible to phosphorylate nucleoside analogs such as aciclovir or ganciclovir, in the same way as HSV1-TK, as is demonstrated later in Example 2 and reference 15.

This property of phosphorylation of the nucleotide analogs by the truncated HSV1-TK HSV1-ΔTK) has the surprising feature that it manifests itself only in the case where the expression, that is to say the transcription and translation of the gene, is strong. On the other hand, if the expression of the gene is weak, then the residual enzyme synthesized is incapable of phosphorylating the nucleotide analogs, contrary to the complete HSV1-TK protein (see FIGS. 2, 3 and 5) (15).

Various methods in the gene therapy-based treatments have already been described above as being specific for the activation of the gene thus transfected both in the case of cells infected with HIV, where a transactivation of the LTR gene by the virus itself is involved as has been described in patent application PCT WO93/08844, and in the case of cancer cells, where the activation is thought to result from the abnormal division of cells which is thought to activate a promoter specific to cancer cells controlling the HSV1-ΔTK gene.

The construct of the invention and especially the nature of the promoter in 5' of the HSV1-TK coding sequence will be chosen according to the use which it is desired to make of the conditional toxicity of the HSV1-ΔTK gene in the presence of nucleoside analogs; for example, in the treatment of cells which are infected or which are capable of being infected by HIV an LTR type promoter from HIV, especially HIV1 or HIV2, will be preferably chosen which contains in 3' a sequence capable of being transactivated by TAT of the TAR type as described in patent WO 93/08844.

If on the other hand, it is desired to carry out a gene therapy for cancer cells, an LTR can be advantageously used which is derived from the Moloney virus and especially from the Mov3 and/or Mov9 and/or Mov13 variants as described by Caruso et al., 1993 (8).

What is unexpected in the construct of the invention is the double characteristic of the HSV1-ΔTK gene to:

on the one hand, express a kinase activity capable of phosphorylating the nucleoside analogs, such as ACV or GCV, and on the other hand, to exhibit this activity only when the truncated thymidine kinase is strongly expressed; to express strongly means that there is at least about fifty transcripts per cell.

This double property exists regardless of the vector into which the gene is integrated and regardless of the transcriptional promoter placed in 5' of this gene.

The construct of the invention containing the HSV1-ΔTK gene may be introduced into any packaging cell line described in the state of the art and especially that mentioned above: these packaging cell lines containing a construct of the invention are capable of transferring the active ingredient of a drug which is toxic in the presence of nucleoside analogs for dividing cells and especially cancer cells. The packaging cell lines transformed by a recombinant vector containing the thymidine kinase gene carrying a deletion upstream of the 2nd ATG initiation codon encoding the methionine in position 46 of the whole protein form part of the invention.

The same is true of the cell lines producing a retrovirus in which the env gene has been deleted in its entirety, or partially, and substituted by HSV1-ΔTK and a nucleic acid sequence including a sequence encoding an envelope protein, which sequence is under the control of a promoter and is associated, where appropriate, with said transgene, and flanked at its 3' end a polyadenylation site said recombinant viral genome and said sequence being capable of transcomplementation and of allowing said host cell to produce infectious viruses lacking the env gene, the whole forming a host vector system which could be injected as it is into tumor cells.

The recombinant pseudoviral sequence contained in the cell line may be derived from an Moloney MuLV genome or from that of an HIV virus.

In the case of treatment of cells which divide little but which are capable of being infected by a virus, especially hematopoietic cells, said cells can be transfected by a construct containing an HSV1-ΔTK sequence, under the control of a promoter specific to the virus capable of infecting said cells, for example HIV and the T lymphocytes, the construct comprising, in addition, a gene capable of being transactivated by TAT, causing the activation of the promoter and of the transcription of the gene in the presence of an infectious virus. The population of cells, especially cells which are hematopoietic and contain the type of construct of the invention, also form part of the invention.

The abovementioned characteristic of the construct containing HSV1-ΔTK of phosphorylating the nucleoside analogs when the transcription is activated and of not phosphorylating them when the expression is weak, has the consequence that in the latter case, the cells expressing said suicide gene are insensitive to the N.As and especially GCV at doses of between 0 and 10 microMolar, whereas after transactivation the cells are sensitive to doses of between $10^{-2}$ and $10^{-1}$ microMolar of GCV. The cell populations which may thus be transfected and contain the constructs of the invention may be:

either cells of the lymphocytic line which are capable of being infected especially by an HIV, in which case the promoter may be an HIV LTR, or T lymphocytes, it being possible for the promoter capable of being transactivated to be a cytokine promoter, or alternatively bone marrow stem cells.

The invention also relates to:

the use, for the production of medicaments intended for the prevention or treatment of diseases induced by viruses, especially pathogenic retroviruses having a specific tropism for certain types of cells, especially hematopoietic cells, of a construct carrying a suicide gene under the control of a specific transactivable promoter, characterized in that said suicide gene is the HSV1-TK thymidine kinase gene deleted of all or part of the 5' sequence upstream of the second ATG initiation codon corresponding to methionine 46 of the complete protein, in particular when the deletion includes all or part of the 1st initiation codon corresponding to methionine No. 1, said retroviral vector being introduced by any appropriate means into said cells;

the use, for the production of active medicaments for inducing a tolerance to antigens and preventing or treating a graft rejection by gene therapy, of a recombinant construct carrying an HSV1-ΔTK gene;

the use, for the production of medicaments intended for the gene therapy-based treatment of cancer, of an appropriate recombinant construct carrying the same HSV1-ΔTK gene;

the use of this type of construct to generate transgenic mice expressing the HSV1-TK activity but, because of the deletion in the 5' region of the gene, the specific activation observed in the transgenic animals at the level of their testicles making these animals sterile is suppressed because of the deletion of the region in question.

The invention relates to a process for the preparation of a recombinant viral vector carrying a suicide gene under the control of a specific transactivable promoter, the toxicity of the product of the gene in the presence of nucleoside analogs depending on said transactivation, characterized in that the suicide gene is an HSV1 thymidine kinase (HSV1-TK) gene deleted in its 5' part of all or part of the sequence upstream of the second ATG initiation codon corresponding to methionine 46 of the complete protein, in particular when the deletion includes all or part of the 1st initiation codon corresponding to methionine No. 1.

Finally, the invention relates to the same HSV1-TK thymidine kinase gene truncated in its 5' region of all or part of the sequence upstream of the second ATG initiation codon corresponding to methionine 46 of the complete protein, in particular when the deletion includes all or part of the 1st initiation codon corresponding to methionine No. 1 and capable of conserving a nucleoside analog phosphorylation activity and exhibiting a conditional toxicity in the presence of GCV above 10 microMolar of analogs, when said gene is weakly expressed and exhibiting a conditional toxicity between $10^{-2}$ and $10^{-1}$ microMolar of N.A., essentially GCV when the gene is activated.

The experiments below will make it possible to illustrate, in different cases, this surprising capacity of the truncated HSV1 thymidine kinase gene and will make it possible, with the aid of the figures, to show the superiority of the use of the HSV1-ΔTK gene in place of HSV1-TK whenever a risk of residual toxicity may lead practitioners to reject the use of the complete gene, when they consider that the risk/benefit ratio is not in favor of the treatment for a given pathology.

BRIEF DESCRIPTION OF THE FIGURES

FIG. 3 represents the profiles obtained by FPLC of the different phosphorylated forms of GCV, after cellular transfection by a construct comprising HSV1-TK (FIG. 3a), a construct HSV1-ΔTK not having been transactivated and therefore having been weakly expressed (3b) and a construct HSV1-ΔTK transactivated by Tat (FIG. 3c).

FIG. 4 represents the sensitivity to ganciclovir of bone marrow cells cultured in the presence of GM-CSF and previously transfected with a construct containing HSV1-TK (black squares) or HSV1-ΔTK (-ΔTK40 and -ΔTK72) under the control of the HIV-LTR.

MATERIALS AND METHODS a) Construction

All the clonings and subclonings were carried out using the customary techniques as described in Maniatis et al. (1989 Molecular cloning laboratory, Coldspring Harbour Laboratory, Coldspring Harbour, N.Y.).

The HSV1-TK gene or HSV1-ΔTK gene were integrated into a plasmid under the control of the HIV 5' LTR according to the experimental procedure described by Caruso et al. 1992 (7) and by Salomon et al. 1995 (15). The LTR exhibits two remarkable characteristics:

being a weak promoter under our experimental conditions, being easily transactivable by the Tat protein.

For the construction of the plasmid p LTR-ΔTK, a ΔTK sequence is amplified by PCR using the TK gene as template. The pair of primers used for the PCR amplification is the following:

a) the 5' oligonucleotide of sequence: 5'CCGAAT-TCAAGCTTATGCCCACGCTACTGCCGG3' contains an EcoR1 site and a HindIII site, stuck to the sequence downstream of the 2nd ATG initiation codon of TK indicated in bold type;

b) the 3' oligonucleotide of sequence 5'CCGGATCCAC-CCGTGCGTTTTATTCTGTCT3' containing the BamHI site, stuck to the sequence surrounding the second polyadenylation site of TK itself indicated in bold type. A 1.05 Kb PCR fragment is then digested with HindIII and Bam HI and ligated downstream of the HIV LTR sequence of the plasmid p LTR-TK deleted of the TK sequence by a HindIII and Bam HI digestion. The retroviral plasmid pNCTat was constructed by insertion of the cDNA fragment obtained by digestion with Bam HI of the Tat fragment of the plasmid pCV-1 as described by Arya et al. (12) downstream of a cytomegalovirus early immediate promoter of the vector pNC. The latter has the neomycin gene and the cytomegalovirus promoter between the two LTRs of the MLV Moloney virus.

The plasmid may also contain in 3' of LTR the HIV TAR gene.

The constructs used will be chosen according to the use which it is desired to make of the toxicity of the suicide gene. In the use as anticancer agents, the plasmid pMTK as described in Caruso et al. 1993(8) will be preferably used.

Persons skilled in the art will know on a case by case basis how to choose the host vector system which they find suitable and are integrated here with reference to all the types of constructs of HSV1-TK which are mentioned above in the state of the art.

b) Deletion of the 5' Part of the HSV1-TK Gene for Obtaining HSV1-ΔTK

Figure 1:
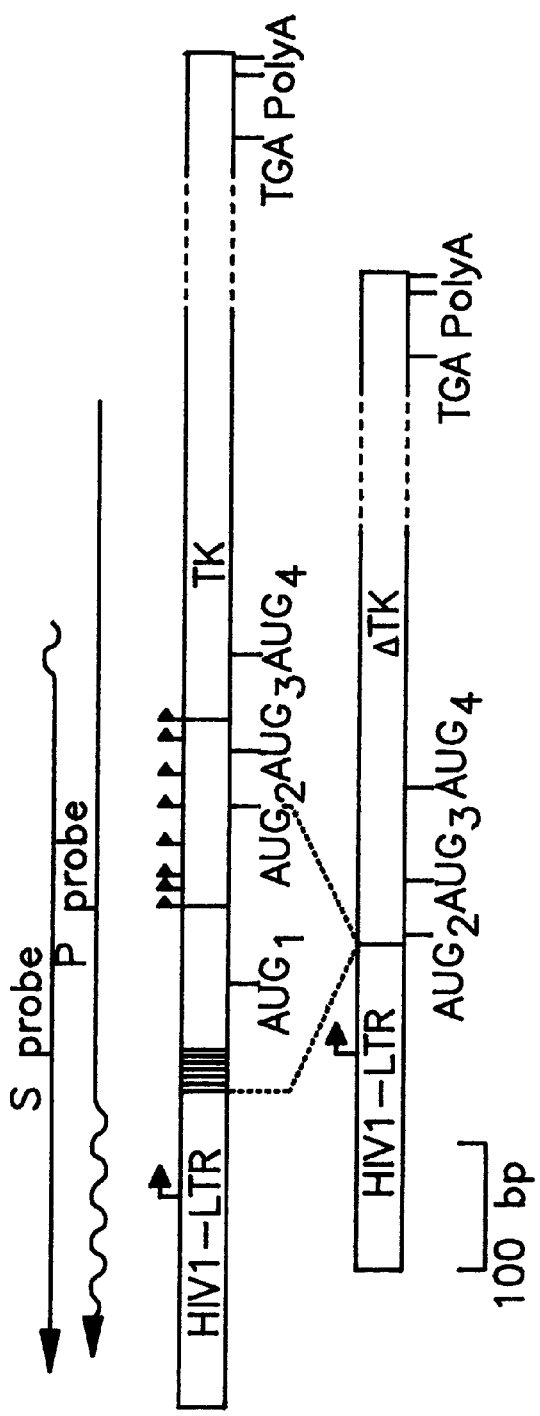
FIG. 1a is a representation of the construct of the invention containing in 5' the HIV LTR and containing, downstream and in the 5'⇒3' direction the TAR sequence (inducible by TAT) of HIV and the HSV1-TK gene.
FIG. 1b represents the construct of the invention deleted of the region upstream of the 2nd ATG codon.

The deletion represented in FIG. 1 and explained above is made by the action of the restriction enzymes HindIII and Bam HI.

c) Evaluation of the Size of the Short Transcripts under the Control of the Cryptic Promoter Deleted in the Construct of the Invention The presence of a cryptic promoter in the sequence coding of HSV1-TK was initially suggested by a Northern-Blot analysis; in the transfection experiments with an HSV1-TK gene lacking a promoter and then selection according to the criterion for obtaining a functional protein, Roberts et al. (13) detected two transcripts of 1.1 Kb and 0.9 Kb. Moreover, Al Shawi et al. (14) detected transcripts in the testicles of transgenic mice carrying the HSV1-TK gene.

The technique used by the patent applicants is the RPA for "RNase Protection Assay" technique which technique made it possible to analyze the presence and the length of the short transcripts in the testicles of transgenic mice expressing HSV1TK, by hybridization with a previously established RNA probe as indicated below and then treatment with Rnase as described in Salomon et al. 1994(10).

The first probe used, called S riboprobe in FIG. 1, has been described in Salomon et al. (10);

The second probe, called riboprobe P in FIG. 1, was obtained in the following manner; a BglII-SacI restriction fragment of HSV1-TK thymidine kinase was integrated into the plasmid PGEM3Z marketed by the company Promega; PGEM-TK was then linearized with the enzyme PvuII and then T7 RNA polymerase was used on the linearized PGEM-TK to finally give the riboprobe P.

d) Cell Culture and Transfection

The culture of the L cells and the transfection of said cells was carried out according to the technique described in Salomon et al. (10).

e) Cell Proliferation and Viability Tests

The measurement of cell proliferation and of the viability of the cells after transfection by the plasmids containing HSV1-TK or HSV1-ΔTK and then treatment by the nucleoside analog was carried out by counting live cells which exclude trypan blue.

EXAMPLE 1

Ganciclovir Sensitivity of L Cells Transfected with a Construct Containing HSV1-ΔTK The constructs carrying the LTR-ΔTK or the control LTR-TK were first transfected into L cells deficient in cellular thymidine kinase and selected by the presence of a functional thymidine kinase by HAT selection.

Clones of cells transfected by LTR-TK grow normally in the selection medium whereas the clones of cells transfected by LTR-ΔTK appear transiently and then die during the second week in selective medium.

The L cells deficient in cellular thymidine kinase were again co-transfected with a plasmid expressing hygromycin and the construct LTR-ΔTK. The different clones were selected in a medium containing hygromycin.

The clone C1 stably transfected by LTR-ΔTK was then infected by a retrovirus expressing the HIV TAT protein (obtained from the retroviral plasmid pNCTat) which transactivates the HIV LTR in 5' of the ΔTK, and then a selection is carried out in HAT.

Different clones were thus selected and then tested for their sensitivity to ganciclovir.

Figure 2:
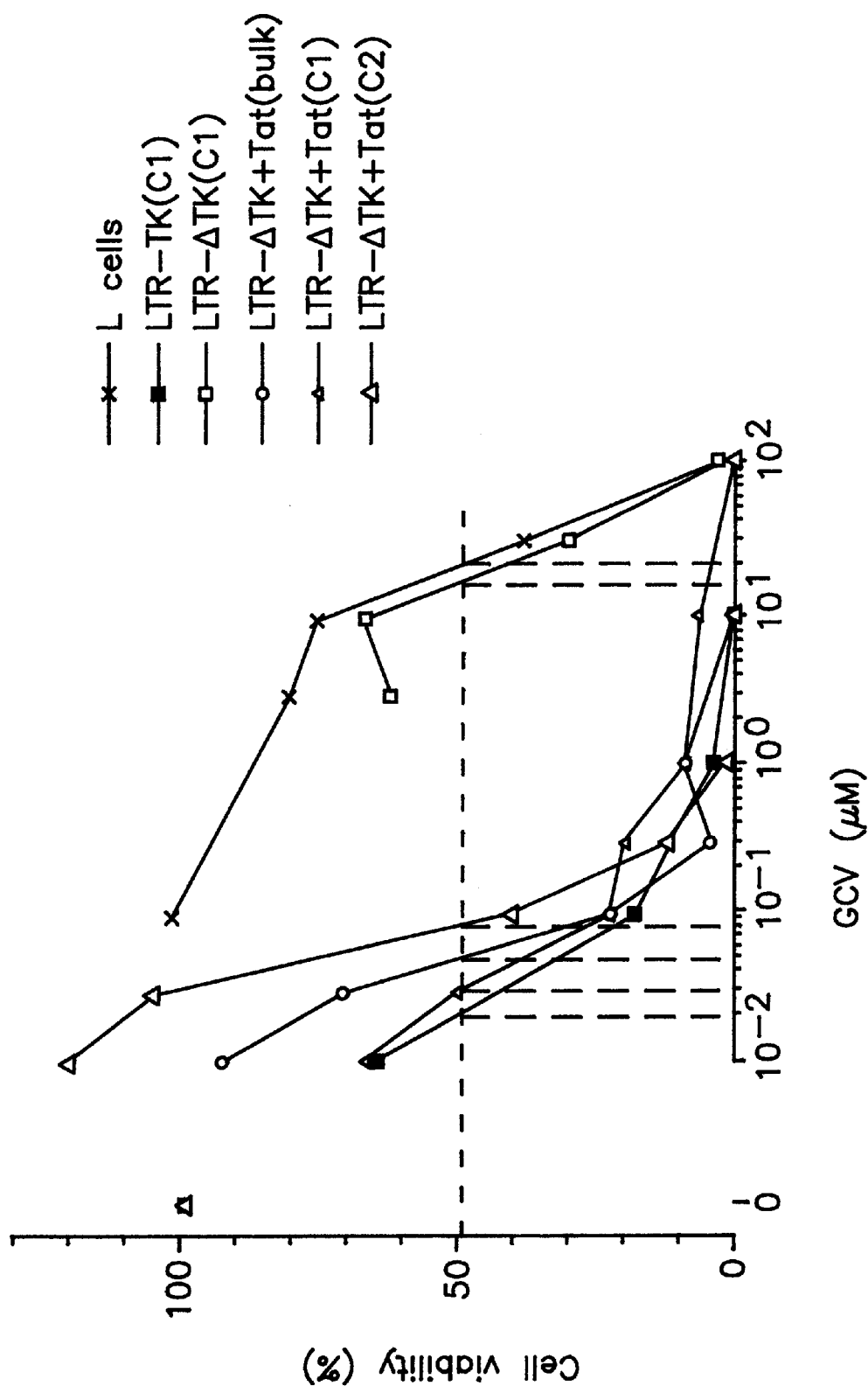
FIG. 2 represents the toxicity of increasing doses of ganciclovir on cells expressing the HSV1-TK or HSV1-ΔTK under the control of the HIV gene LTR (LTR-TK or LTR-ΔTK) in the absence or presence of Tat. The sign C1 indicates that the 1st clone of the cell line was used, C2 referring to a 2nd clone and "bulk" to a mixture or to the noncloned line.

In FIG. 2, it can be seen that the inhibitory dose 50% (ID50) of GCV is 20 μM for the parental L cells and 0.02 μM for the LTR-TK clones C1 and C2.

The ID50 for the LTR-ΔTK clone (C1) is 20 μM, namely the same GCV sensitivity as the parental cells whereas the ID50 of two tested clones HSV1-ΔTK+TAT is between 0.03 and 0.08 μM.

It can therefore be deduced from this figure that the truncated thymidine kinase has the same efficiency as the normal thymidine kinase when the gene is activated (LTR-ΔTK+TAT), whereas at a weak level of expression, that is to say without transactivation by TAT, the level of sensitivity to ganciclovir is identical as that found in the control cells lacking the TK or ΔTK gene.

Moreover, we verified this observation on human HeLa cells in the absence of HAT selection. The clones expressing LTR-ΔTK which are transactivated by Tat and are obtained only after selection in hygromycin are killed at GCV concentrations of less than 0.1 μM.

EXAMPLE 2

FPLC Analysis of the Degree of Phosphorylation of Ganciclovir

FIG. 3 shows the profiles obtained after FPLC chromatography (Pharmacia) of the lysates of L cells transfected either by LTR-TK (FIG. 3a), or by LTR-ΔTK (FIG. 3c) or by LTR-ΔTK+TAT (FIG. 3b)

Examination of the figure indicates that the chromatographic profiles are similar in the first two cases (3a and 3b), whereas in the presence of a transactivation of the truncated gene, the phosphorylation activity of the truncated thymidine kinase is similar to that of the nontruncated thymidine kinase: the respective percentages of GCV, GCV monophosphate, diphosphate and triphosphate are comparable.

In contrast, in the absence of transactivation, the LTR-ΔTK is weakly expressed and the cellular lysate contains only GCV, with the exclusion of the phosphorylated forms.

EXAMPLE 3

Transfection of the LTR-ΔTK Gene into Mouse Lines thirteen transgenic lines carrying LTR-ΔTK were prepared, the males in all these lines being fertile and transmitting the transgene to their progeny according to a Mandelian transmission.

No HSV1-ΔTK short transcript could be detected by the RPA test described above in the testicles.

Six of the eight transgenic lines analyzed for the expression of the transgene have a significant level of LTR-ΔTK transcripts in the skin, which is comparable to the level of TK transcripts in the LTR-TK transgenic mice described above (10).

The functionality of this expression of the truncated thymidine kinase was tested for possible depletion in dendritic cells in said transgenic mice.

Bone marrow cells were cultured in the presence of GM-CSF for 6 days, which makes it possible to generate proliferative dendritic cells.

The GCV sensitivities of the bone marrow dendritic cells obtained from transgenic mice either carrying LTR-TK, or carrying LTR-ΔTK, are compared in FIG. 4; the results obtained with the transgenic lines 40 and 72 carrying LTR-ΔTK are represented therein.

The ID50 is 40 μM for the nontransgenic mice, 0.035 μM for the transgenic lines containing the complete LTR-TK gene, 2 μM for the transgenic line LTR-ΔTK 72 and 20 μM for the line LTR-ΔTK 40.

GCV was administered, in addition, to mice of 12 different transgenic lines: the dose of 20 to 50 mg per kilo and per day which was used for the removal of the cells in the transgenic line LTR-TK 14 has no effect on the LTR-ΔTK line; only the high doses of GCV (70 to 120 mg per kilo and per day) which are nontoxic for nontransgenic mice have a moderate effect on 6 of these lines.

The dendritic cells are partially depleted since they represent 0.4 to 0.9% of the splenocytes; this is in comparison with the 1.5% obtained with nontransgenic mice.

Figure 5A:
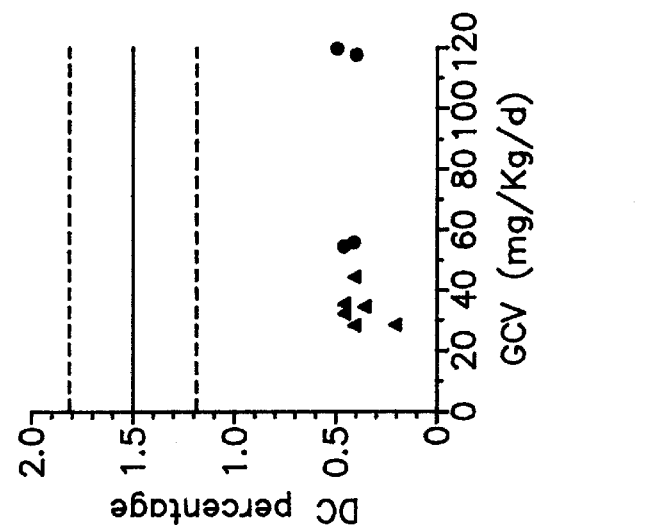
FIG. 5 represents the effect of GCV in vivo on control mice (□), transgenic mice weakly expressing TK (transgenic mice in which TK is under the control of HIV-LTR (▲) weakly expressing Δ-TK (transgenic mice in which Δ-TK is under the control of HIV-LTR) (■), strongly expressing Δ-TK (transgenic mice in which Δ-TK is under the control of HIV-LTR are crossed with transgenic mice expressing Tat under the control of a ubiquitous promoter (●). The graphs show the depletions of the dendritic cells obtained after 7 days of treatment with GCV expressed in mg/kg/day.
Figure 5B:
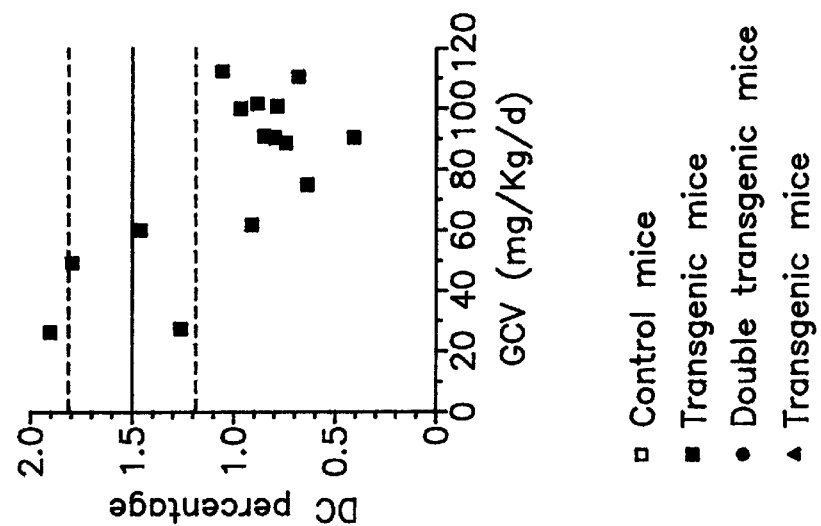
Figure 5C:
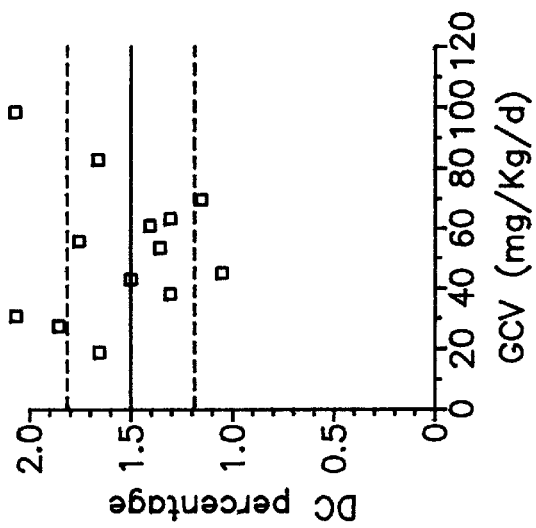

In the LTR-ΔTK mice, the expression of ΔTK is very weak and explains the partial depletion of the dendritic cells. In order to increase the expression of ΔTK, we crossed our LTR-ΔTK transgenic mice with transgenic mice expressing the Tat gene under the control of an ubiquitous promoter. The double transgenic mice treated with GCV have a depletion of the dendritic cells in the spleen which is equivalent to the LTR-TK transgenic mice treated with GCV as shown in FIG. 5.

All these experiments show that the cells expressing low doses of HSV1-TK remain sensitive to the toxic effect of GCV whereas the cells expressing HSV1-ΔTK at a low dose are not sensitive to GCV.

The whole advantage of the constructs of the invention appears clear by virtue of the above experiments, especially as regards the safety and the reduction in the risks of this type of treatment for patients, since only one situation of active transcription of the gene confers on the suicide gene its conditional toxicity. In the case of a weak expression (or nontransactivation of the promoter), the truncated gene is incapable of phosphorylating the nucleotide analogs and therefore they exhibit no toxicity for the cells, even in the presence of these analogs.

Suicide gene-based gene therapy can thus be envisaged in the case where the risk/benefit evaluation might become unfavorable with the use of the complete gene.

REFERENCES (1) Furman et al. (1980) Virology 102: 420–430.
(2) St Clair et al. (1987) Antimicrobial Agents Chemotherapy 31: 844–849
(3) Moolten F. L. (1986) Cancer Research, 46:5276–5281
(4) Culver K. W. et al. (1992) Science 256:1550–1552)
(5) Venkatesh et al. (1990)—Proc. natl. acad. sciences 1990 87:8746–8750
(6) M. Muesing et al; (1987) Tat, 48:691–701
(7) Caruso et al. (1992) Proc. Natl. Acad. Sci. U.S.A., 89:182
(8) Caruso et al. (1993) Proc. Natl. Acad. Sci. U.S.A., 90:7024–7028
(9) Panis Y et al. (1992) C. R. Acad Sci. Paris, t. 315 serie IIIp 541–543
(10) Salomon B et al. (1994) J. of Immunol. 152:537–548
(11) Elion G. B. et al. (1983) J. Antimicrobi Chemother 12: 9–17
(12) Arya et al. (1985) Science 229:69–73
(13) Roberts et al. (1982) Cell 29:109–119
(14) Al-Shawi et al. (1991) Mol. Cel. Biol. 11:4207–4216
(15) Salomon et al. (1995) Mol. Cel. Biol. 15. In Press.

We claim:

1. A recombinant vector comprising:
a gene encoding a Herpes Simplex Virus Type 1 thymidine kinase (HSV1-TK) comprising a deletion in the 5' sequence upstream of the second ATG initiation codon of the complete HSV1-TK, wherein said gene is under the control of a promoter, wherein said deletion is sufficient to inhibit transcription initiation from a cryptic promoter site contained within said 5' sequence, and wherein the HSV1-TK produced by the expression of said gene is toxic to cells in the presence of nucleoside analogs when said gene is strongly expressed.

2. The recombinant vector according to claim 1, wherein said deletion comprises all or part of the first initiation codon.

3. The recombinant vector according to claim 1 or 2, wherein said vector is selected from HIV or MoMuLV.

4. The recombinant vector according to claim 3, wherein said promoter is an HIV LTR.

5. The recombinant vector according to claim 4, wherein said HIV LTR is an HIV1 LTR or and HIV2 LTR.

6. The recombinant vector according to claim 3, wherein said promoter is a Moloney Virus LTR.

7. The recombinant vector according to claim 6, wherein said Moloney Virus is MOV3, MOV9 or MOV13.

8. A packaging cell line transduced by a recombinant retro viral vector according to claim 3.

9. A cell line transfected with a viral vector comprising a substitution of the env gene by a gene encoding a Herpes Simplex Virus Type 1 thymidine kinase (HSV1-TK) operatively linked 5' to promoter, and wherein said HSV1-TK is further operatively linked 3' to a polyadenylation site, and wherein said HSV1-TK comprises a deletion in the 5' sequence upstream of the second ATG initiation codon of the complete HSV1-TK, wherein said gene is under the control of a retroviral LTR, and wherein the HSV1-TK produced by the expression of said gene is toxic to cells in the presence of nucleoside analogs when said gene is strongly expressed.

10. The cell line according to claim 9, wherein said deletion comprises all or part of the first initiation codon.

11. The cell line according to claim 9, wherein said viral vector is selected from MoMuLV or HIV.

12. An isolated population of mammalian bone marrow cells comprising a gene encoding a Herpes Simplex Virus Type 1 thymidine kinase (HSV1-TK) comprising a deletion in the 5' sequence upstream of the second ATG initiation codon of the complete HSV1-TK, wherein said gene is under the control of an LTR and wherein said bone marrow cells after transactivation strongly express said gene resulting in cell toxicity.

13. The isolated cell population according to claim 12, wherein said deletion comprises all or part of the first initiation codon.

14. The isolated population according to claim 12 or 13, wherein said transactivation comprises infecting said cells by a retrovirus which provides TAT.

15. The isolated population according to claim 12, wherein GM-CSF has been added to culture media.

16. A gene encoding a Herpes Simplex Virus Type 1 thymidine kinase (HSV1-TK) comprising a deletion in the 5' sequence upstream of the second ATG initiation codon of the complete HSV1-TK, wherein said deletion is sufficient to inhibit transcription initiation from a cryptic promoter site contained within said 5' sequence, and wherein the HSV1-TK produced by the expression of said gene is toxic to cells in the presence of nucleoside analogs when said gene is strongly expressed.

17. The gene according to claim 16, wherein said deletion comprises all or part of the first initiation codon.

* * * * *